| United States Patent [19] | [11] | 4,268,520 |
|---|---|---|
| Grantham | [45] | May 19, 1981 |

[54] INSECTICIDAL AND NEMATICIDAL CARBAMATES

[75] Inventor: Gary D. Grantham, Newark, Del.

[73] Assignee: E. I. Du Pont de Nemours and Company, Wilmington, Del.

[21] Appl. No.: 151,901

[22] Filed: May 21, 1980

Related U.S. Application Data

[62] Division of Ser. No. 899,298, Apr. 24, 1978, Pat. No. 4,225,615.

[51] Int. Cl.² .................... A01N 43/12; C07D 307/86
[52] U.S. Cl. .................................... 424/285; 424/267; 424/274; 260/326.34; 260/346.73; 546/196
[58] Field of Search ............... 260/326.34, 346.73; 546/196; 424/267, 274, 285

[56] References Cited

U.S. PATENT DOCUMENTS 4,169,894 10/1979 D'Silva .................. 260/346.73

FOREIGN PATENT DOCUMENTS 1297095 of 0000 Fed. Rep. of Germany .
2654246 of 0000 Fed. Rep. of Germany .
2654282 of 0000 Fed. Rep. of Germany .
2654313 of 0000 Fed. Rep. of Germany .
2654314 of 0000 Fed. Rep. of Germany .

Primary Examiner—Henry R. Jiles
Assistant Examiner—Bernard Dentz

[57] ABSTRACT

N,N'-[Alkanediylbis(oxycarbonyliminothio)]bis-[carbamates], such as N,NPR-[1,2-ethanediylbis(thio-N-methyliminocarbonyloxy)]bis[2-(dimethylamino)-2-oxo-]ethanimidothioic acid, dimethyl ester, useful as insecticides and nematicides.

9 Claims, No Drawings

INSECTICIDAL AND NEMATICIDAL CARBAMATES

This is a division, of application Ser. No. 899,298, filed Apr. 24, 1978 now U.S. Pat. No. 4,225,615.

BACKGROUND OF THE INVENTION

This invention relates to insecticidal and nematicidal carbamates.

Insecticidal carbamates are known in the prior art, e.g., (a) German DT No. 2,654,313 which includes disclosure to compounds of the formula

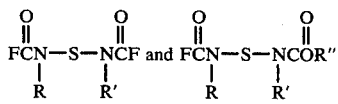

(b) German DT No. 2,654,314 which includes disclosure to compounds of the formula

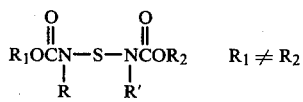

(c) German DT No. 2,654,282 which includes disclosure to compounds of the formula

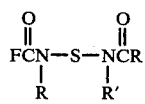

(d) German DT No. 2,654,246 which includes disclosure to compounds of the formula

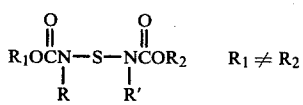

(e) German DT No. 1,297,095 which includes a disclosure to a compound of the formula

In the above publications the various R substituents are widely defined.

SUMMARY OF THE INVENTION

This invention relates to novel compounds of Formula I, to agricultural compositions containing them, and to the method of use of these compounds as insecticides and nematicides.

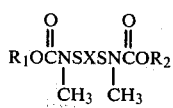

wherein

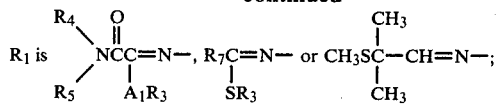

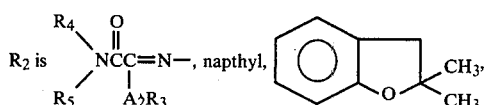

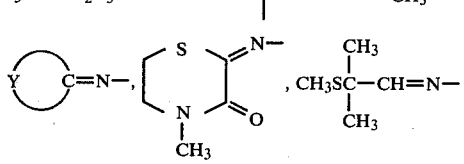

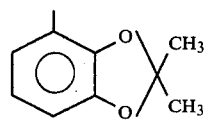

phenyl, or phehyl substituted with one of (a) to (g),
(a) 1-3 methyl groups, (b) $C_3$-$C_5$ branched alkyl, (c) methylthio, (d) dimethylamio, (e) diallylamino, (f) $R_9SCH_2$ wherein $R_9$ is methyl or ethyl, (g) $(CH_3)_2NCH{=}N$;

wherein $Y$ is a divalent aliphatic chain, a divalent aliphatic chain with one or two divalent sulfur, sulfoxide or sulfone groups.

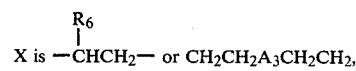

$R_3$ L is alkenyl, alkynyl of three or four carbons, or alkyl or one to four carbons;

$R_4$ and $R_5$ are independently alkyl of one to four carbons, $CH_3O$, or cycloalkyl of three to five carbons or $R_4$ and $R_5$ are taken together to form an alkylene bridge of four to six carbons;

provided that $R_4$ and $R_5$ contakin a total of not more than seven carbons and that $R_4$ and $R_5$ are not both simultaneously $OCH_3$ or both cycloalkyl;

$R_6$ is hydrogen or methyl;

$R_7$ is alkyl of 1-4 carbons; and $A_1$, $A_2$ and $A_3$ are independently oxygen or sulfur.

DETAILED DESCRIPTION OF THE INVENTION

Preferred Compounds

Preferred because of their high activity and/or favorable cost are compounds of Formula I wherein

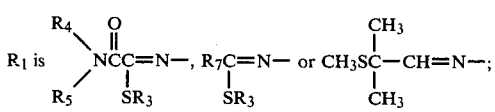

$R_3$ is alkyl of 1-3 carbons;
$R_4$ and $R_5$ are $CH_3$;
$R_7$ is alkyl of 1-2 carbons, and
$X$ is —$CH_2CH_2$—.

Equally preferred for their high activity and/or favorable cost are compounds of formula I wherein $R_2$ is $$\begin{matrix} R_4 & O \\ \diagdown & \| \\ N-CC=N-, \\ \diagup & | \\ R_5 & SR_3 \end{matrix}$$ naphthyl,

[benzofuran structure with CH$_3$, CH$_3$, CH$_3$ substituents]

$$\begin{matrix} & CH_3 & \\ & | & \\ CH_3S-&C&-CH=N-; \\ & | & \\ & CH_3 & \end{matrix}$$

phenyl or phenyl substituted with one of (a) to (c), (a) 1–3 carbons, (b) branched alkyl $C_3$–$C_5$, or (c) methylthio;

$R_3$ is alkyl of 1–3 carbons;
$R_4$ and $R_5$ are $CH_3$; and
X is —$CH_2CH_2$—.

More preferred for their higher activity and/or more favorable cost are comounds of formula I wherein $$R_1 \text{ is } (CH_3)_2N\underset{\underset{SR_3}{|}}{\overset{\overset{O}{\|}}{C}}C=N-, \quad R_7\underset{\underset{SR_3}{|}}{C}=N- \text{ or } CH_3S\underset{\underset{CH_3}{|}}{\overset{\overset{CH_3}{|}}{C}}-CH=N-;$$

$$R_2 \text{ is } (CH_3)_2N\underset{\underset{SR_3}{|}}{\overset{\overset{O}{\|}}{C}}C=N- \text{ or } CH_3S\underset{\underset{CH_3}{|}}{\overset{\overset{CH_3}{|}}{C}}CH=N-;$$

wherein
$R_3$ is alkyl of 1–2 carbons, and
X is —$CH_2CH_2$—.

Most preferred for their outstanding activity and/or even more favorable cost and/or ease of synthesis are those compounds of the more preferred class wherein $R_1 = R_2$.

Specifically preferred for their very outstanding activity and/or most favorable cost are N,NPR-[1,2-Ethanediylbis(thio-N-methyliminocarbonyloxy)]bis[2-(dimethylamino)-2-oxo-]ethanimidothic acid, dimethyl ester, 2-(Dimethylamino)-N-[[[[N-methyl-N-[[[2-[[N-methyl-N-[(1-methylthioethylidene)aminooxycarbonyl-]aminothio]]-ethylthio]]]aminocarbonyloxy]]]]-2-oxoethanimidothioic acid, methyl ester, 2-(Dimethylamino)-N-[[[[N-methyl-N-[[[-2-[[N-methyl-N-[(2-methyl-2-methylthio-propylidene)aminooxycarbonyl]-aminothio]]ethylthio]]]aminocarbonyloxy]]]]-2-oxoethanimidothioic acid, methyl ester.

Preparation

The compounds of Formula I wherein $R_1 = R_2$ can be prepared, as shown in Equation A, by reacting two moles of an acid ester of Formula II with one mole of an alkane disulfenyl halide of Formula III in the presence of base:

Equation A $$2R_1O\overset{\overset{O}{\|}}{C}\underset{\underset{CH_3}{|}}{N}H + ZSXSZ \xrightarrow{\text{base}} R_1O\overset{\overset{O}{\|}}{C}\underset{\underset{CH_3}{|}}{N}SXS\underset{\underset{CH_3}{|}}{N}\overset{\overset{O}{\|}}{C}OR_1 \quad (I, R_1 = R_2)$$

(II)   (III)

wherein $R_1$ and X are as previously defined and Z is halogen.

The reaction can be carried out in an inert organic solvent, e.g. methylene chloride, dioxane, tetrahydrofuran, chloroform, 1,2-dichloroethane, benzene, toluene, or the xylenes. Mixtures of these solvents can also be used.

Organic or inorganic bases which can function as an acid acceptor can be used, e.g. pyridine.

The process can be carried out at a temperature between about $-20°$ and $60°$ C., preferably between about $-5°$ and $40°$ C. Pressure is not critical, for convenience atmospheric pressure is preferred.

Compounds of Formula I in which $R_1$ and $R_2$ are the same or different can also be prepared, as shown in Equation B, by reacting two moles of methyl carbamoyl fluoride with one mole of an alkane disulfenyl halide of Formula III in the presence of base to afford compounds of Formula IV, which are then reacted sequentially (in the presence of base) with one mole of $R_1OH$ and one mole of $R_2OH$ wherein $R_1$, $R_2$, and X are as previously defined and Z is halogen.

Equation B $$CH_3NH\overset{\overset{O}{\|}}{C}F + ZSXSZ \xrightarrow{\text{base}} FC\underset{\underset{CH_3}{|}}{N}SXS\underset{\underset{CH_3}{|}}{N}\overset{\overset{O}{\|}}{C}F \quad (IV)$$

(III)

$\Big\downarrow R_1OH, \text{base}$ $$R_1O\overset{\overset{O}{\|}}{C}\underset{\underset{CH_3}{|}}{N}SXS\underset{\underset{CH_3}{|}}{N}\overset{\overset{O}{\|}}{C}OR_2 \xleftarrow{\underset{\text{base}}{R_2OH}} R_1O\overset{\overset{O}{\|}}{C}\underset{\underset{CH_3}{|}}{N}SXS\underset{\underset{CH_3}{|}}{N}\overset{\overset{O}{\|}}{C}F$$

(I)

The reactions can be carried out in an inert organic solvent, e.g. benzene, toluene, the xylenes, tetrahydrofuran, dioxane, methylene chloride, chloroform, 1,2-dichloroethane, or lower alcohols such as methanol and ethanol. Mixtures of these solvents can also be used.

Organic or inorganic bases which can function as an acid acceptor can be used, e.g. pyridine.

The first step of the process can be carried out at a temperature between about $-30°$ C. and $0°$ C., preferably between about $-25°$ C. and $-15°$ C. The later steps of the process can be carried out at a temperature between about $-20°$ and $100°$ C., preferably between about $-5°$ and $40°$ C. Pressure is not critical; for convenience atmospheric pressure is preferred.

In the compounds of Formula III chlorine is the preferred halogen for economic reasons, and these compounds can be prepared by a suitable modification of the method described for preparing ethane-1,2-disulfenyl chloride in *Journal of Heterocyclic Chemistry*, 6, 629 (1969). Alkane sulfenyl halides such as those of Formula III wherein Z is fluorine, bromine, or iodine are also known and may be prepared by the methods reviewed by *Synthesis*, 11, 561–580 (1970).

The synthesis of methyl carbamoyl fluoride used as a starting material in Equation B is described in Belgian Pat. Nos. 843,415 and 843,416.

Acid esters of Formula II can be synthesized by the reaction of methyl isocyanate with the appropriate phenol, e.g. U.S. Pat. No. 2,903,478, or by the reaction of methyl isocyanate with the appropriate oxime, e.g., U.S. Pat. Nos. 3,576,834; 3,639,633; 3,530,220; and 3,658,870.

The compound of formula IV and its method of preparation are disclosed and claimed in concurrently filed Application Ser. No. 899,299, filed Apr. 24, 1979, and now U.S. Pat. No. 4,127,605.

In the following examples, all parts are by weight and temperatures are in degrees centigrade unless otherwise specified.

EXAMPLE 1

N,N'-[1,2-Ethanediylbis(thio-N-methyliminocarbonyloxy)]-bis-[2-(dimdethylamino)-2-oxo] ethanimidothioic acid, dimethyl ester A solution of 65.8 g of 2-(dimethylamino)-N-[[(methylamino)carbonyl]oxy]-2-oxoethanimidothioic acid, methyl ester and 32.6 g of ethane-1,2-disulfenyl chloride in 150 ml of methylene chloride was prepared and cooled to 0° C. To this solution was added dropwise with stirring 32.0 ml of pyridine over a period of 45 minutes, keeping the temperature of the reaction mixture at 0° C. with external cooling. After addition was complete, the reaction mixture was allowed to warm to ambient temperature and stirring was continued for 16 hours. Pyridine hydrochloride and other insolubles were then filtered off and the reaction mixture washed twice with water and dried over anhydrous magnesium sulfate. Distillation of the methylene chloride under reduced pressure afforded 80.0 g of a brown viscous resin. The title compound could be isolated from this resin by chromatography on Mallinkrodt CC-7 silica gel using ethyl acetate to elute unreacted starting materials and methanol to elute the title compound. Using this procedure, 30.0 g of resin chromatographed on 1 kg of silica gel afforded 2.0 g of substantially pure N,N'-[1,2-ethanediylbis-(thio-N-methyliminocarbonyloxy)]-bis-[2-(dimethylamino)-2-oxo] ethanimidothioic acid, dimethyl ester m.p. 130°–135° C. (decomposes). Calculated for $C_{16}H_{28}N_6O_6S_4$: C, 36.35; H, 5.34; N, 15.90; S, 24.26; Found: C, 34.92; H, 5.1; N, 15.05; S, 23.44. A purer sample can be obtained by recrystallization from an appropriate solvent.

EXAMPLE 2

N,N'-[[1,2-Ethanediylbis(thio)]bis[N-methyl-]] carbamic fluoride

A solution of 10.2 g of ethane-1,2-disulfenyl chloride in 175 ml toluene was prepared and cooled to −35° C. under a nitrogen atmosphere. To this solution was added in one portion 9.7 g of N-methylcarbamyl fluoride. To the reaction solution was added dropwise over 0.5 hr a solution of 12.7 g of triethylamine in 30 ml toluene, maintaining the temperature of the reaction mixture between −30° C. to −25° C. After addition was complete, the reaction mixture was stirred 0.5 hr at −30° C. to −25° C.; then allowed to warm to ambient temperature. The reaction mixture was washed with three 200 ml portions of water and dried over anhydrous magnesium sulfate. Distillation of the toluene under reduced pressure gave a brown oil which crystallized on standing. The title compound was isolated from the crude reaction product by recrystallization from 1-chlorobutane employing decolorizing charcoal. There was obtained 2.2 g of N,N'-[[1,2-ethanediylbis(thio)]bis[N-methyl-]] carbamic fluoride, mp 88°–90.5° C. Calculated for $C_6H_{10}F_2N_2O_2S_2$: C, 29.50; H, 4.13; N, 11.47; S, 26.25. Found: C, 31.14; H, 4.38; N, 11.31; S, 26.34; C, 30.58; H, 4.24; N, 11.53; S, 26.01.

EXAMPLE 3

N,N'-[1,2-Ethanediylbis(thio-N-methyliminocarbonyloxy)]bis[2-(dimethylamino)-2-oxo-] ethanimidothioic acid, dimethyl ester ;P A solution of 2.44 g of N,N'-[[1,2-ethanediyl-bis(thio)]-bis[N-methyl-]] carbamic fluoride and 3.24 g of 2-(dimethylamio)-N-hydroxy-2-oxoethanimidothioic acid, methyl ester in 125 ml tetrahydrofuran was prepared. To this solution was added dropwise at ambient temperature a solution of 2.02 g of triethylamine in 10 ml tetrahydrofuran. After addition was complete, the reaction mixture was stirred 45.5 hr at ambient temperature. The solvent was distilled under reduced pressure to afford a yellow reside. The residue was dissolved in 100 ml methylene chloride, and the organic solution was washed with two 300 ml portions of water, a 150 ml, portion of saturated sodium chloride solution, and dried over anhydrous magnesium sulfate. Distillation of the methylene chloride at reduced pressure afforded a viscous, yellow oil which partially solidified on scratching. The gummy solid was suspended in 50 ethanol and the white solid was collected, washed with a few ml of ethanol, and dried giving 1.5 g of N,N'-[1,2-ethanediyl-bis(thio-N-methyliminocarbonyloxy)]bis[2-(dimethylamino-2-oxo]ethanimidothioic acid, dimethyl ester, mp 156°–160° C. Calculated for $C_{16}H_{28}N_6O_6S_4$: C, 36.35; H, 5.34; N, 15.90; S, 24.26. Found: C, 36.4; H, 5.60; N, 15.8; S, 24.2.

EXAMPLE 4

2-(Dimethylamino)-N-[[[N-[[2-[N-(fluorocarbonyl)-N-methylaminothio]ethylthio]]-N-methylaminocarbonyloxy]]]-2-oxoethanimidothioic acid, methyl ester A solution of 2.44 g of N,N'-[[1,2-ethanediyl-bis(thio)]bis[N-methyl-]] carbamic fluoride and 1.62 g of 2-(dimethylamino)-N-hydroxy-2-oxoethanimidothioic acid, methyl ester was prepared in 75 ml of tetrahydrofuran. To this solution was added dropwise at ambient temperature a solution of 1.01 g of triethylamine in 10 ml tetrahydrofuran. After addition was complete, the reaction mixture was stirred 22 hr at ambient temperature. The solvent was distilled under reduced pressure, and the residual yellow oil was dissolved in 100 ml methylene chloride. The organic solution was washed with two 150 ml portions of water, a 150 ml portion of saturated sodium chloride, and dried over anhydrous magnesium sulfate. Distillation of the methylene chloride under reduced pressure gave a viscous pale yellow oil. The title compound was isolated from the crude reaction product by chromatography on Mallindrodt CC-7 silica gel. Elution with ethyl acetate gave 1.4 g of 2-(dimethylamino)-N-[[[N-[[2-[N-(fluorocarbonyl)-N-methylaminothio]ethylthio]]-N-methylaminocarbonyloxy]]]-2-oxoethanimidothioic acid, methyl ester as a viscous, pale yellow oil. Calculated for $C_{11}H_{19}FN_4O_4S_3$- C, 34.18; H, 4.95; N, 14.50; S, 24.89. Found: C, 34.7; H, 5.29; N, 15.5; S, 25.2; C, 35.4; H, 5.09; N, 14.5; S, 25.7.

EXAMPLE 5

2-(Dimethylamino)-N-[[[[N-methyl-N-[[[2-[[N-methyl-N-[(1-metylthioethylidene)aminooxycarbonyl]aminothio]]-ethylthio]]]aminocarbonyloxy]]]]-2-oxoethanimidothioic acid, methyl ester A solution of 0.8 g of N-hydroxy-ethanimidothioic acid, methyl ester in 5 ml methanol and 10 toluene was prepared, 0.4 g of sodium methoxide was added in one portion, and the mixture was stirred until dissolution was complete. The solution of the sodium salt of N-hydroxy-ethanimidothioic acid was added dropwise at 0° C. to a solution of 3.0 g of 2-(dimethylamino)-N-[[[N-[[2-[N-(fluorocarbonyl)-N-methylaminothio]ethylthio]]-N-methylaminocarbonyloxy]]]-2-oxoethanimidothioic acid, methyl ester in 100 ml toluene. The resulting turbid reaction mixture was allowed to warm to ambient temperature and stirred 18 hrs. The reaction mixture was washed with two 100 ml portions of water, 100 ml of saturated sodium chloride solution, and dried over magnesium sulfate. Distillation of the solvent under reduced pressure gave a pale yellow viscous oil. The title compound was isolated from the crude reaction product by chromatography on silica gel employing ethyl acetate to elute the product. Using this procedure there was obtained 1.4 g of an oil that partially solidified. Suspension of the oily solid in a mixture of ether and hexanes gave 1.3 g of substantially pure 2-(dimethylamino)-N-[[[[N-methyl-N-[[[2-[[-N-methyl-N-[(1-methylthioethylidene)aminooxycarbonyl]aminothio]]ethylthio]]]aminocarbonyloxy]]]]-2-oxoethanimidothioic acid, methyl ester, m.p. 102°-106° C.

Calculated for $C_{14}H_{25}N_5O_5S_4$: C, 35.65; H, 5.34; N, 14.85; S, 27.19; Found: C, 36.6; H, 5.44; N, 14.8; S, 26.2 C, 36.0; H, 5.25; N, 14.6 S, 26.1

EXAMPLE 6

2-(Dimethylamino)-N-[[[[N-methyl-N-[[[2-[[N-methyl-N-[(1-naphthalenyloxy)carbonyl]aminothio]]ethylthio]]]-aminocarbonyloxy]]]]-2-oxoethanimidothioic acid, methyl ester A solution of 0.7 g of 1-naphthol in 50 ml toluene was prepared and cooled to 0° C. A 10 ml portion of 0.5 molar sodium methoxide in methanol was added dropwise, and mixture stirred several minutes. Approximately one-half of the solvent were distilled under reduced pressure. The resulting suspension was diluted with 25 ml toluene and 2 ml tetrahydrofuran, and the solution was cooled to 0° C. A solution of 1.9 g of 2-(dimethylamino)-N-[[[N-[[2-[N-(fluorocarbonyl)-N-methylaminothio]ethylthio]]-N-methylaminocarbonyloxy]]]-2-oxoethanimidothioic acid, methyl ester in 40 ml toluene was added dropwise over 0.5 hr at 0° C. After addition was complete, the reaction mixture was stirred 1 hr at 0° C., then allowed to warm to ambient temperature. The reaction mixture was heated on a steam bath 1 hr, then stirred overnight at ambient temperature. The reaction mixture was washed with two 100 ml portions of water, a 100 ml portion of saturated sodium chloride, and dried over anhydrous magnesium sulfate. Distillation of the solvent under reduced pressure gave a brown oil. The title compound was isolated by subjecting the crude reaction product to two chromatographies on silica gel employing ethyl acetate to elute the product. Using this procedure there was obtained 0.6 g of glassy 2-(dimethylamino)-N-[[[[N-methyl-N-[[[2-[[N-methyl-N-[(1-naphthalenyloxy)carbonyl]aminothio]]ethylthio]]]-aminocarbonyloxy]]]]-2-oxoethanimidothioic acid, methyl ester.

Calculated for $C_{21}H_{26}N_4O_5S_3$: C, 49.39; H, 5.13; N, 10.97; S, 18.84; Found: C, 49.1; H, 5.05; N, 11.0; S, 19.4 C, 48.7; H, 5.52; N, 10.7; S, 19.9.

By reacting equivalent amounts of other compounds according to Equations A and B using the procedures of Examples 1 through 6, the following compounds of Formula I can be prepared:

TABLE 1

$$\left[ \begin{array}{c} R_4 \\ \diagdown \\ N-C=N-OC-NS \\ \diagup \quad | \quad | \\ R_5 \quad AR_3 \quad CH_3 \end{array} \begin{array}{c} O \quad O \\ \| \quad \| \\ \\ \\ \end{array} \right]_2 X$$

| R4 | R5 | A | R3 | X |
|---|---|---|---|---|
| CH3 | C2H5 | S | CH3 | —CH2CH2— |
| CH3 | C3H7 | S | CH3 | CH2CH2 |
| CH3 | i-C3H7 | S | CH3 | CH2CH2 |
| CH3 | C4H9 | S | CH3 | CH2CH2 |
| CH3 | CH3O | S | CH3 | CH2CH2 |
| ⬠ | CH3 | S | CH3 | CH2CH2 |
| C4H9 | CH3 | O | CH3 | CH2CH2 |
| △ | CH3 | S | CH3 | CH2CH2 |
| CH3 | CH3 | S | CH3 | —CH—CH2 with CH3 branch |
| CH3 | CH3 | S | CH3 | —CH2CH2OCH2CH2— |
| CH3 | CH3 | S | CH3 | —CH2CH2SCH2CH2— |
| C2H5 | C2H5 | S | CH3 | —CH2CH2— |
| C3H7 | C3H7 | S | CH3 | —CH2CH2— |
| CH3 | CH3 | S | C2H5 | —CH2CH2— |
| CH3 | CH3 | S | C3H7 | —CH2CH2— |
| CH3 | CH3 | S | C4H9 | —CH2CH2— |
| CH3 | CH3 | O | CH3 | —CH2CH2— |
| CH3 | CH3 | O | CH3 | —CH2CH2OCH2CH2— |
| CH3 | CH3 | S | CH2=CHCH2— | —CH2CH2— |

TABLE 1-continued $$\left[ \begin{array}{c} R_4 \\ \diagdown \\ R_5 \end{array} N-\underset{AR_3}{\overset{\underset{\displaystyle \|}{O}}{C}}=N-O\overset{\underset{\displaystyle \|}{O}}{C}-N\underset{CH_3}{S} \right]_2 X$$

| R4 | R5 | A | R3 | X |
|---|---|---|---|---|
| CH3 | CH3 | S | CH2=CCH2–<br>\|<br>CH3 | –CH2CH2– |
| CH3 | CH3 | S | CH≡C–CH2– | –CH2CH2– |
| CH3 | CH3 | S | CH3C≡CCH2– | –CH2CH2– |
| –CH2CH2CH2– | | S | CH3 | –CH2CH2– |
| –CH2CH2CH2CH2– | | S | CH3 | –CH2CH2– |
| –CH2(CH2)3CH2– | | S | CH3 | –CH2CH2– |
| –CH2(CH2)4CH2– | | S | CH3 | –CH2CH2– |

TABLE II $$\underset{R_3}{\overset{R_4}{\diagdown}} N\underset{}{\overset{\underset{\displaystyle \|}{O}}{C}}-\underset{AR_3}{C}=N O \overset{\underset{\displaystyle \|}{O}}{C}-\underset{CH_3}{N}-S-X-S-\underset{CH_3}{N}-\overset{\underset{\displaystyle \|}{O}}{C}-O-R_2$$

| R3 | R4 | A | R3 | X | R2 |
|---|---|---|---|---|---|
| CH3 | CH3 | S | CH3 | –CH2CH2– | 3,5-dimethyl-4-(diallyl-amino)phenyl |
| " | " | " | " | " | 3-methyl-4-dimethylamino)phenyl |
| " | " | " | " | " | 2-sec-butylphenyl |
| " | " | " | " | " | 4-methylthiophenyl |
| " | " | " | " | " | 2-(1,3-dioxalan-2-yl)phenyl |
| " | " | " | " | " | 3-methyl-4-methylthiophenyl |
| " | " | " | " | " | 3-dimethylaminomethylene-iminophenyl |
| " | " | " | " | " | 2-isopropylphenyl |
| " | " | " | " | " | 3,5-dimethyl-4-methylthiophenyl |
| " | " | " | " | " | 3-(1-methylbutyl)phenyl |
| " | " | " | " | " | 3-(1-ethylpropyl)phenyl |
| " | " | " | " | " | 3,5-dimethyl-4-dimethyl-aminophenyl |
| " | " | " | " | " | 3-isopropyl-5-methylphenyl |
| " | " | " | " | " | 3-methylphenyl |
| " | " | " | " | " | 3,4-dimethylphenyl |
| " | " | " | " | " | 3,5-dimethylphenyl |
| " | " | " | " | " | 1-naphthyl |
| " | " | " | " | " | 2-methylthiomethylphenyl |
| " | " | " | " | " | 2-ethylthiomethylphenyl |
| " | " | " | " | " | 2,3-dihydro-2,2-dimethyl benzofuran-7-yl |
| " | " | " | " | " | 2,3-isopropylidenedioxy-phenyl |
| " | " | " | " | " | –N=CHC(CH3)2SCH3 |

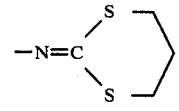

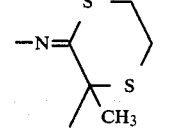

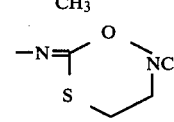

TABLE III $$R_6 \overset{\underset{\displaystyle \|}{O}}{C}=NO\overset{}{C}N-\underset{CH_3}{S}-X-S N\overset{\underset{\displaystyle \|}{O}}{C}-OR_2$$
$$\phantom{R_6C=NOCN} \underset{AR_3}{|} \phantom{-S-X-SN} \underset{CH_3}{|}$$

| R6 | A | R3 | X | R2 |
|---|---|---|---|---|
| CH3 | S | CH3 | CH2CH2 | 3,5-dimethyl-4-(diallylamino)phenyl |
| " | " | " | " | 3-methyl-4-(dimethylamino)phenyl |
| " | " | " | " | 2-sec-butylphenyl |
| " | " | " | " | 4-methylthiophenyl |
| " | " | " | " | 2-(1,3-dioxalan-2-yl)phenyl |
| " | " | " | " | 3-methyl-4-methylthiophenyl |
| " | " | " | " | 3-dimethylaminomethyleneimino-phenyl |
| " | " | " | " | 2-isopropylphenyl |
| " | " | " | " | 3,5-dimethyl-4-methylthiophenyl |
| " | " | " | " | 3-(1-methylbutyl)phenyl |
| " | " | " | " | 3-(1-ethylpropyl)phenyl |
| " | " | " | " | 3,5-dimethyl-4-dimethylaminophenyl |
| " | " | " | " | 3-isopropyl-5-methylphenyl |
| " | " | " | " | 3-methylphenyl |
| " | " | " | " | 3,4-dimethylphenyl |
| " | " | " | " | 3,5-dimethylphenyl |
| " | " | " | " | 1-naphthyl |
| " | " | " | " | 2-methylthiomethylphenyl |
| " | " | " | " | 2-ethylthiomethylphenyl |
| " | " | " | " | 2,3-dihydro-2,2-dimethylbenzofuran- |

TABLE III-continued $$R_6C=NOCN-S-X-SNC-OR_2$$
with $\underset{AR_3}{|}$ $\underset{CH_3}{|}$ on left N, $\underset{CH_3}{|}$ on right N, and =O above each C

| $R_6$ | A | $R_3$ | X | $R_2$ |
|---|---|---|---|---|
| " | " | " | " | 7-yl |
| " | " | " | $-CH_2CH_2-$ | 2,3-isopropylidenedioxyphenyl |
| " | " | " | " | $-N=CHC(CH_3)_2SCH_3$ |
| " | " | " | " | $-N=C\diagup^S\diagdown_S$ (cyclic) |
| " | " | " | " | $-N=\underset{CH_3}{\underset{|}{C}}-\underset{CH_3}{\underset{|}{C}}-S$ (cyclic with S) |
| " | " | " | " | $-N=\underset{S}{\overset{O}{C}}\diagup\diagdown NCH_3$ (ring) |
| $C_2H_5$ | S | $CH_3$ | $CH_2CH_2$ | $-N=\underset{SCH_3}{\underset{|}{C}}-\overset{O}{\underset{||}{C}}N(CH_3)_2$ |
| $C_3H_7$ | " | $CH_3$ | $CH_2CH_2$ | " |
| $CH_3$ | " | $C_2H_5$ | $CH_2CH_2$ | " |
| $CH_3$ | " | $CH_3H_7$ | $CH_2CH_2$ | " |
| $CH_3$ | " | $C_4H_9$ | $CH_2CH_2$ | " |
| $CH_3$ | " | $CH_2=CHCH_2$ | $CH_2CH_2$ | " |

TABLE IV $$R_1-OCN-SX-SN-\overset{O}{\underset{||}{C}}-OR_2$$
with $\underset{CH_3}{|}$ on each N, and =O above left C

| $R_1$ | $R_2$ |
|---|---|
| $CH_3S\underset{\underset{CH_3}{\|}}{\overset{\overset{CH_3}{\|}}{C}}-CH=N-$ | $-N=CH\underset{\underset{CH_3}{\|}}{\overset{\overset{CH_3}{\|}}{C}}-SCH_3$ |
| " | $-N=C-\overset{O}{\underset{\|\|}{C}}N(CH_3)_2$ with $SCH_3$ |
| " | $-N=C\diagup^S\diagdown_S$ |
| " | $-N=C\diagup^S\diagdown$ ring with $O=$, $N-CH_3$ |

Formulation

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

|  | Percent by Weight | | |
|---|---|---|---|
|  | Active Ingredient | Diluent(s) | Surfactant(s) |
| Wettable Powders | 20–90 | 0–74 | 1–10 |
| Oil Suspensions Emulsions, Solutions, (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins et al, "Handbook of Insecticide Dust Diluents and Carriers", 2nd Edn., Dorland Books, Caldwell, N.J. The more absorptive diluents are preferred for wettable powders and the denser ones for dusts. Typical liquid diluents and solvents are described in Marsden, "Solvents Guide", 2nd Edn., Interscience, New York, 1950. Solubility under 0.1% is preferred for suspension concentrates; solution concentrates are preferably stable against phase separation at 0° C. "McCutcheon's Detergents and Emulsifiers Annual", McCutcheon Division, MC Publishing Co., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. 3,060,084). Granules and pellets may be made by spraying the active material upon preformed granular carriers or by agglomeration techniques.

See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8–59ff.

For further information regarding the art of formulation, see for example:

J. B. Buchanan, U.S. Pat. No. 3,576,834 Apr. 27, 1971, Col. 5, line 36 through Col. 7, line 70 and Exs. 1–4, 17, 106, 123–140.

R. R. Shaffer, U.S. Pat. No. 3,560,616, Feb. 2, 1971, Col. 3, line 48 through Col. 7, line 26 and Exs. 3–9, and 11–18.

E. Somers, "Formulation", Chapter 6 in Torgeson, "Fungicides", Vol. I, Academic Press, New York, 1967.

EXAMPLE 7

Wettable Powder

| | |
|---|---|
| N,NPR-[1,2-Ethanediylbis(thio-N-methyliminocarbonyloxy)]bis-[2-(dimethylamino)-2-oxo-] ethanimidothioic acid, dimethyl ester | 40.0% |
| dioctyl sodium sulfosuccinate | 1.5% |
| sodium ligninsulfonate | 3.0% |
| low viscosity methyl cellulose | 1.5% |
| attapulgite | 54.0% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 8

Wettable Powder

| | |
|---|---|
| 2-(Dimethylamino)-N-[[[[N-methyl-N-[[[2-[[N-methyl-N-[(1-methylthioethylidene)amino-oxy-carbonyl]aminothio]]ethylthio]]]aminocarbonyloxy]]]]-2-oxoethanimidothioic acid, methyl ester | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE 9

Aqueous Suspension

| | |
|---|---|
| 2-(Dimethylamino)-N-[[[[N-methyl-N-[[[2-[[N-methyl-N-[(2-methyl-2-methylthiopropylidene)-aminooxycarbonyl]aminothio]]ethylthio]]]-aminocarbonyloxy]]]]-2-oxoethanimidothioic acid, methyl ester | 25.0% |
| hydrated attapulgite | 3.0% |
| crude calcium ligninsulfonate | 10.0% |
| sodium dihydrogen phosphate | 0.5% |
| water | 61.5% |

The ingredients are ground together in a ball or roller mill until the solid particles have been reduced to diameters under 10 microns.

EXAMPLE 10

Oil Suspension

| | |
|---|---|
| N,NPR-[1,2-Ethanediylbis(thio-N-methyliminocarbonyloxy)]bis-[2-(dimethylamino)-2-oxo-] ethanimidothioic acid, dimethyl ester | 25.0% |
| polyoxyethylene sorbitol hexaoleate | 5.0% |
| highly aliphatic hydrocarbon oil | 70.0% |

The ingredients are ground together in a sand mill until the solid particles have been reduced to under about 5 microns. The resulting thick suspension may be applied directly, but preferably after being extended with oils or emulsified in water.

EXAMPLE 11

Granule

| | |
|---|---|
| Wettable powder of Example 8 | 7.7% |
| attapulgite granules (U.S.S. No. 20–40; 0.84–0.42 mm) | 92.3% |

A slurry of wettable powder containing 50% solids is sprayed on the surface of attapulgite granules in a double-cone blender. The granules are dried and packaged. They contain 5% active ingredient.

EXAMPLE 12

Extruded Pellet

| | |
|---|---|
| 2-(Dimethylamino)-N-[[[[N-methyl-N-[[[2-[[N-methyl-N-[(1-methylthioethylidene)amino-oxy-carbonyl]aminothio]]ethylthio]]]aminocarbonyloxy]]]]-2-oxoethanimidothioic acid, methyl ester | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

The ingredients are blended, hammer-milled and then moistened with about 12% water. The mixture is extruded as cylinders about 3 mm diameter which are cut to produce pellets about 3 mm long. These may be crushed to pass a U.S.S. No. 20 sieve (0.84 mm opening). The granules held on a U.S.S. No. 40 sieve (0.42 mm opening) may be packaged for use and the fines recycled.

EXAMPLE 13

High-Strength Concentrate

| | |
|---|---|
| N,NPR-[1,2-Ethanediylbis(thio-N-methyliminocarbonyloxy)]bis-[2-(dimethylamino)-2-oxo-] ethanimidothioic acid, dimethyl ester | 98.5% |
| silica aerogel | 0.5% |
| synthetic amorphous fine silica | 1.0% |

The ingredients are blended and ground in a hammer mill to produce a high-strength concentrate essentially all passing a U.S.S. No. 50 sieve (0.3 mm opening). This material may then be formulated in a variety of ways.

EXAMPLE 14

Dust

| | |
|---|---|
| High-strength concentrate, Example 13 | 25.4% |
| prophyllite, powdered | 74.6% |

The ingredients are thoroughly blended and packaged for use.

EXAMPLE 15

Emulsifiable Concentrate

| | |
|---|---|
| 2-(Dimethylamino)-N-[[[[N-methyl-N-[[[2-[[N-methyl-N-[(2-methyl-2-methylthiopropylidene)-aminooxycarbonyl]aminothio]]ethylthio]]]-aminocarbonyloxy]]]]-2-oxoethanimidothioic acid, methyl ester | 15.0% |
| chlorobenzene | 79.0% |
| sorbitan monostearate and polyoxyethylene condensates thereof | 6.0% |

The ingredients are combined and stirred to produce a solution which can be emulsified in water for application.

Use

The compounds of this invention are useful for control of insects which are detrimental to agriculture and public health. They readily control pestiferous insects belonging to such orders as Homoptera, Coleoptera and Diptera. More specifically, pests controlled by the compounds of this invention include but are not limited to: aphids (*Aphis Fabae*), flies (*Musca domestica*), boll weevil (*Anthonomoss grandis*) and mites (*Tetranychus Urticae*).

The insects are controlled by applying the material in a convenient formulation to the locus of infestation, to the area to be protected, or to the pests themselves. For the control of insects in agricultural crops, the compound is generally applied to the foliage or other plant parts which are infested or which are to be protected. Effective amounts to be applied depend upon the species to be controlled, its life stage, its size and location, the amount of rainfall, the time of year, moisture, temperature, type of application, and other variables. In general, 0.1 to 10 kg/ha may be required for insect control in agriculture with rates of 0.25 to 5 kg/ha usually being sufficient. Preferred rates in large-scale operations are in the range of ½ to 2 kg/ha. Where penetration of the insect cuticle is needed for activity, addition of an adjuvant which acts as a penetrant may be beneficial.

The compounds of this invention are also useful for control of nematodes detrimental to agriculture. They readily control but are not limited to the rootknot nematode, *Meloidogyne incognita*. The plant parasitic nematodes are controlled by applying the material in a convenient formulation to infested soil prior to planting. Rates of 0.25 to 50 kilograms per hectare are most preferred.

Other methods of applying the compound include: spraying above ground parts of plants such as stems, leaves or buds in which nematodes are present or where later attack is possible; dipping or soaking reproductive parts such as seeds, slips or bulbs. Rates of active ingredient in the sprays or dips are 30 grams to 1.2 kilograms per 100 liters.

The compounds of this invention will generally be used in formulation with a carrier that commonly will consist of oil or water. Applications may be made with concentrated or dilute solutions or suspensions of the active compound in the carrier. Low volume applications utilizing suspensions containing 18.75% of the active ingredient may be preferred by some applicators while others may prefer dilute solutions or suspensions containing only 80 ppm in high-volume applications.

The compounds of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the compound of this invention may vary from 0.0625 to 25 parts by weight. Suitable agents of this type are well known to those skilled in the art. Some are listed below:

Fungicides methyl 2-benzimidazolecarbamate
tetramethyl thiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
N-trichloromethylthiotetrahydrophthalimide (captan)
N-trichloromethylthiophthalimide (folpet)

Bactericides:

tribasic copper sulfate
streptomycin sulfate

Acaricides:

senecioic acid, ester with 2-sec-butyl-4,6-dinitrophenol ("Morocide")
6-methyl-1,3-dithiolo[2,3-β]quinonolin-2-one ( "Morestan")
ethyl 4,4'-dichlorobenzilate (Chlorobenzilate ®)
1,1-bis(p-chlorophenyl)-2,2,2-trichloroethanol (Kelthane ®)
bis(pentachloro-2,4-cyclopentadine-lyl) (Pentac ®)
tricyclohexyl tinhydroxide (Plictran ®)

Nematicides:

S-methyl 1-(dimethylcarbamoyl)-N-(methylcarbamoyloxy)-thioformimidate (Vydate ®)
S-methyl 1-carbamoyl-N-(methylcarbamoyloxy)thioformimidate
N-isopropylphosphoramidic acid, O-ethyl-O'-[4-(methylthio)-m-tolyl]diester ("Nemacur")

Insecticides:

3-hydroxy-N-methylcrotonamide (dimethylphosphate)ester (Azodrin ®)
methylcarbamic acid, ester with 2,3-dihydro-2,2-dimethyl-7-benzofuranol (Furadan ®)

O-[2,4,5-trichloro-α-(chloromethyl)benzyl]phosphoric acid, O',O'-dimethyl ester (Gardona®)

2-mercaptosuccinic acid, diethyl ester, S-ester with thionophosphoric acid, dimethyl ester (Malathion®)

phosphorothioic acid, O,O-dimethyl, O-p-nitrophenyl ester (methyl parathion)

methylcarbamic acid, ester with α-naphthol (Sevin®)

methyl O-(methylcarbamoyl)thiolacetohydroxamate (methomyl)

N'-(4-chloro-o-tolyl)-N,N-dimethylformamidine (Galecron®)

O,O-diethyl-O-(2-isopropyl)-4-methyl-6-pyrimidylphosphorothioate (Diazinon®)

octachlorocamphene (toxaphene)

O-ethyl O-p-nitrophenyl phenylphosphonothioate (EPN)

cyano (3-phenoxyphenyl)methyl-4-chloro-α-(1-methylethyl)-benzeneacetate (Pyridin®)

(3-phenoxyphenyl)methyl(+)-cis,trans-3-(2,2-dichloroethenyl)-2,2-dimethylcyclopropanecarboxylate (Ambush®)

O-ethyl-S-(p-chlorophenyl)ethylphosphonodithioate (Curacron®)

phosphorothiolothionic acid, O-ethyl-O-[4-(methylthio)-phenyl]-S-n-propyl ester (Bolstar®)

The following examples illustrate use of the compounds of this invention.

EXAMPLE 16

N,NPR- [1,2-Ethanediylbis(thio-N-methyliminocarbonyloxy)]bis[2-(dimethylamino)-2-oxo]ethanimidothioc acid, dimethyl ester was mixed into soil containing root-knot nematode, *Meloidogyne incognita,* and the soil was planted with cucumber seeds. After two weeks, the roots were examined for nematode injury and the results are summarized below.

| Rate, kg/ha | % Nematode Control |
|---|---|
| 10 | 100 |
| 3 | 100 |
| 1 | 100 |
| 0.5 | 100 |
| 0.25 | 77 |
| Untreated control | 0 |

EXAMPLE 17

Excised nasturtium leaflets infested with all stages of the black bean aphid were placed in small bottle-like vases. Cotton placed in the neck of the bottle holds the stem firmly in place and prevents spray from entering the bottle. These test units were then sprayed to run-off with a dispersion of N,NPR-[1,2-Ethanediylbis(thio-N-methyliminocarbonyloxy)]bis-[2-(dimethylamino)-2-oxo-]ethanimidothioic acid, dimethyl ester made by dissolving appropriately weighed samples in 10 ml of acetone and then diluted to 100 ml with water containing Duponol L-144-WDG at 1:3000. The test units were then maintained under artificial lights at 77°±2° F. and 55±5% relative humidity for approximately 24 hours prior to evaluation. Percent mortality for various concentrations of the spray dispersions recorded below.

| Spray Concentration (ppm) | % Mortality |
|---|---|
| 10,000 | 100 |
| 2,000 | 100 |
| 500 | 96 |
| 100 | 85 |

"Consisting essentially of" is intended to have its customary meaning: namely, that all specified materials and conditions are very important in practicing the invention but that unspecified materials and conditions are not excluded so long as they do not prevent the benefits of the invention from being realized.

I claim:

1. A compound of the formula $$R_1OCNSXSNCOR_2$$

with two C=O groups and CH$_3$ substituents on the N atoms:

$$\underset{CH_3}{R_1O-\overset{O}{\overset{\|}{C}}-N}-S-X-S-\underset{CH_3}{N-\overset{O}{\overset{\|}{C}}-OR_2}$$

wherein $R_1$ is 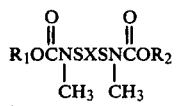, $R_7C=N-$ with $SR_3$, or $$CH_3S\overset{CH_3}{\underset{CH_3}{\overset{|}{C}}}-CH=N-;$$

$R_2$ is 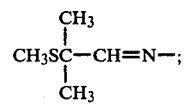, napthyl,

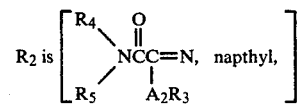

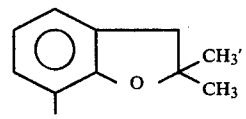

wherein

X is $-CHCH_2-$ with $R_6$ substituent, or $CH_2CH_2A_3CH_2CH_2$;

$R_3$ is alkenyl, alkynyl of three or four carbons, or alkyl of one to four carbons;

$R_4$ and $R_5$ are independently alkyl of one to four carbons, $CH_3O$, or cycloalkyl of three to five carbons or $R_4$ and $R_5$ are taken together to form an alkylene bridge of four to six carbons;

provided that $R_4$ and $R_5$ contain a total of not more than seven carbons and that $R_4$ and $R_5$ are not both simultaneously $OCH_3$ or both cycloalkyl;

$R_6$ is hydrogen or methyl;

$R_7$ is alkyl of 1-4 carbons; and $A_1$ and $A_3$ are independently oxygen or sulfur.

2. A compound of claim 1 wherein $R_1$ is 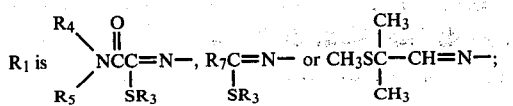

$R_3$ is alkyl of 1-3 carbons;
$R_4$ and $R_5$ are $CH_3$;
$R_7$ is alkyl of 1-2 carbons; and
X is $-CH_2CH_2-$.

3. A compound of claim 1 wherein $R_2$ is

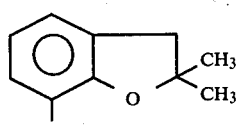

and X is $-CH_2CH_2-$.

4. An insecticidal and nematocidal composition consisting essentially of a diluent, surfactant or mixtures thereof and an insecticidally or nematocidally effective amount of a compound of claim 1.

5. An insecticidal and nematocidal composition consisting essentially of a diluent, surfactant or mixtures thereof and an insecticidally or nematocidally effective amount of a compound of claim 2.

6. An insecticidal and nematocidal composition consisting essentially of a diluent, surfactant or mixtures thereof and an insecticidally or nematocidally effective amount of a compound of claim 3.

7. A method for control of insects or nematodes which comprises applying to a locus to be protected an insecticidally or nematicidally effective amount of a compound of claim 1.

8. A method for control of insects or nematodes which comprises applying to a locus to be protected an insecticidally or nematicidally effective amount of a compound of claim 2.

9. A method for control of insects or nematodes which comprises applying to a locus to be protected an insecticidally or nematicidally effective amount of a compound of claim 3.

* * * * *

UNITED STATES PATENT OFFICE
CERTIFICATE OF CORRECTION

PATENT NO. : 4,268,520
DATED : May 19, 1981
INVENTOR(S) : Gary D. Grantham

It is certified that error appears in the above-identified patent and that said Letters Patent are hereby corrected as shown below:

In claim 1, line 33, delete 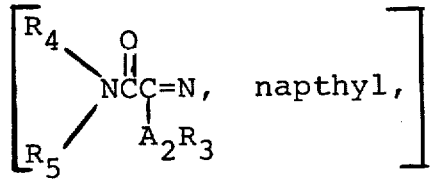

In claim 1, line 45, delete 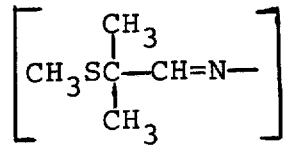

Signed and Sealed this

Twenty-sixth Day of January 1982

[SEAL]

Attest:

Attesting Officer

GERALD J. MOSSINGHOFF

Commissioner of Patents and Trademarks